United States Patent
Harz et al.

[11] Patent Number: 5,972,669
[45] Date of Patent: *Oct. 26, 1999

[54] SALT-STABILIZED ENZYME PREPARATIONS

[75] Inventors: Hans-Peter Harz, Dudenhofen; Roland Jürgen Betz, Niederkirchen, both of Germany

[73] Assignee: Gist-brocades, B.V., Netherlands

[*] Notice: This patent is subject to a terminal disclaimer.

[21] Appl. No.: 09/178,838

[22] Filed: Oct. 26, 1998

Related U.S. Application Data

[63] Continuation of application No. 08/681,792, Jul. 29, 1996, Pat. No. 5,827,709.

[30] Foreign Application Priority Data

Jul. 28, 1995 [EP] European Pat. Off. ............ 95202066

[51] Int. Cl.$^6$ .............................. C12N 9/96; C12N 9/24; C12N 9/00
[52] U.S. Cl. ........................ 435/188; 435/41; 435/183; 435/200; 426/623
[58] Field of Search ............................ 435/41, 183, 188, 435/200; 426/623

[56] References Cited

U.S. PATENT DOCUMENTS

| | | | |
|---|---|---|---|
| 3,515,642 | 6/1970 | Mima et al. | 195/63 |
| 3,616,205 | 10/1971 | Ito | 435/273 |
| 3,674,644 | 7/1972 | Yokotsuka et al. | 435/223 |
| 4,077,842 | 3/1978 | Cory et al. | 195/63 |
| 4,237,231 | 12/1980 | Jackson et al. | 435/234 |
| 4,699,882 | 10/1987 | Visuri | 435/188 |
| 5,449,613 | 9/1995 | Dordick et al. | 435/41 |
| 5,464,766 | 11/1995 | Bruno | 435/183 |
| 5,580,856 | 12/1996 | Prestrelski et al. | 514/21 |

*Primary Examiner*—Leon B. Lankford, Jr.
*Assistant Examiner*—Christopher R. Tate
*Attorney, Agent, or Firm*—Morrison & Foerster LLP

[57] ABSTRACT

The present invention discloses methods to improve the processing and storage stability of dry enzyme preparations. To this extend an inorganic salt, e.g. $MgSO_4$, is dissolved in an enzyme containing solution which is subsequently dried, using e.g. spray drying. Not only does the addition of salt improve the yield of enzyme activity upon drying, also the storage and processing stability of the obtained solid composition containing the enzyme and the inorganic salt are improved with respect to enzyme activity. The invention further discloses solid compositions comprising enzymes and inorganic salts.

15 Claims, No Drawings

SALT-STABILIZED ENZYME PREPARATIONS

This is a continuation of application Ser. No. 08/681,792, filed Jul. 29, 1996, which issued as U.S. Pat. No. 5,827,709.

FIELD OF THE INVENTION

The present invention relates to the conversion of enzyme solutions to solid enzyme preparations with improved drying yield, and storage and processing stability.

BACKGROUND OF THE INVENTION

The width of the application field and therefore the importance of enzymes in modern technology is increasing rapidly. One of the major drawbacks of these compounds however, is their aptitude to deactivation, caused not only by extremes of temperature, pH and the like during processing, but also occurring spontaneously on prolonged storage under otherwise normal conditions.

Often applied methods known in the art to diminish this problem include the use of a variety of additives claimed to stabilize enzymes in solution or the conversion of the enzyme solution to a dry formulation by means of freeze drying, spray drying or other techniques suitable for this purpose. The conversion of an enzyme in solution to a dry form is often obligatory when the application so demands (e.g. convenient mixing with other dry components).

Although drying in itself is a valuable tool in the improvement of the enzyme storage stability, the process step itself often causes a substantial loss of activity and the final product is still susceptible to inactivation. This activity loss during storage or processing is strongly dependent on moisture content of the preparation and this therefore has to be most stringently controlled to maintain the so valued product stability. This also includes a severe reduction of choice in the compounds suited for addition to the final enzyme product for the sake of standardization or other purposes.

In a variety of cases the dry enzyme is intended for applications in which the enzyme has to be incorporated in a product in which the moisture content can not be so strictly controlled. In these cases the enzyme stability is then severely reduced.

Several inventions have been made in the field of stabilizing enzymes against losses during drying and subsequent storage and handling.

The bulk of these inventions (such as presented in the patent (applications) U.S. Pat. No. 3,515,642, EP 0501375A1 and WO 91/14773) are concerned with the addition of carbohydrate and, more specific, sugar or polyol components to the enzyme concentrate.

Also known in the art is the inclusion of components into the formulation with the aim to produce a glassy product at storage temperature, thus improving enzyme stability (EP 0383569A2).

Another approach is the addition to the formulation of one or several components able to bind moisture. This will reduce the water activity of the final preparation or temporarily prevent the interaction of water penetrating from the surroundings with the enzyme itself.

The use of organic and inorganic salts as a processing aid (e.g. to improve flowing behaviour of the product) or bulking/standardizing agent is well known. However, the use of inorganic salts to improve stability of dry enzyme preparations during processing or storage does not appear to be described in the art. In some cases enzyme destabilisation due to salt addition was even specifically mentioned (see e.g. Mikhailova et al. 1989, Vestsi Akad Navuk BSSR, Ser Biyal Navuk 6: 62–65).

EP 0522269A2 discloses the addition of insoluble calcium carbonate to an enzyme solution to be spraydried.

WO 92/11 347 discloses the incorporation of water soluble inorganic salts into enzyme containing granulates. The water soluble inorganic salts must be chosen such that they do not affect the storage stability of the enzyme granulate. WO 92/11347 provides several sodium- and potassium-salts as being suitable for this purpose. The water soluble inorganic salts are however added to the enzymes in dry form prior to their granulation by extrusion.

DESCRIPTION OF THE INVENTION

The present invention provides a method for the production of solid enzyme formulations with improved drying yield and improved storage and processing stability of the resulting products. This is achieved. by preparing a solution comprising an enzyme and a water soluble inorganic salt, preferably an inorganic salt of a divalent cation, more preferably zinc, magnesium or calcium salt, most preferably zinc or magnesium sulphate, and subsequent drying of the product. Also a combination of salts as well as a combination of enzymes can be used for this purpose. Divalent cations are preferred because they provide the best storage and processing stability. Sulphate is preferred as anion because it provides the best drying yield. The invention also provides solid enzyme formulations obtained by preparing a solution comprising an enzyme and a water soluble inorganic salt, preferably an inorganic salt of a divalent cation, more preferably zinc, magnesium or calcium salt, most preferably zinc or magnesium sulphate, and subsequent drying of the solution comprising the enzyme and the water soluble inorganic salt.

In the method of the invention, the salt is present while the enzyme is still in solution, i.e. prior to drying. Not only does this results in a higher yield during drying, but also the storage stability of the obtained dry enzyme preparations is improved as well as their processing stability. Processing stability is herein understood to mean the stability of the enzyme preparation during any handling of the enzyme preparation other than storage, such as e.g. the mixing of the enzyme preparation with other components or during the application of the enzyme.

Drying of the solution containing the enzyme and the salt will result in a solid composition which is homogeneous with respect to the distribution of the enzyme and the salt.

The drying of the enzyme and salt containing solution can be achieved by any drying method available to the skilled person, such as spray-drying, freeze drying, vacuum drying, fluid bed drying, and microwave drying. Drying of the enzyme-salt solution can also be combined with granulation methods which comprise e.g. the use of a fluid bed or a Multi-stage dryer (MSD). In case of the use of these granulation methods, the skilled person will understand that the obtained composition is not necessarily completely homogeneous. The obtained particles will usually consist of agglomerates of homogeneous particles or will consist of coated particles with a homogeneous core, with a homogeneous coating and/or combinations thereof. In any case there will be a homogenous interdispersion of the enzyme and the salt with respect to each other.

The specific examples of the invention demonstrate that the stabilising effect of the salt increases with increasing dosage of the salt to the enzyme solution, until at a certain point further increases in salt dosage no longer produce further improvement of the enzyme stability. For this reason at least 5%, preferably at least 15%, more preferably at least 30%, still more preferably at least 60%, and most preferably at least 90% (w/w) of salt is added to the enzyme solution, wherein the salt dosage is expressed as the weight percentage (w/w) of added salt based on the weight of the enzyme in solution, not including the weight of the crystal water of the salt crystals.

Although there is no upper limit to the addition of the salt from the view of the invention, a physical limit results from the maximum solubility of the salt in the enzyme concentrate. Higher salt/enzyme ratios can then only be realized by dilution of the enzyme solution or the use of a combination of salts.

Another point of consideration might be the dosage at which the enzyme is 'salted out', this being dependent on both the type of salt and the specific enzyme under consideration. Combinations of salts and enzymes giving rise to the 'salting out'-phenomenon are not excluded from the invention.

The invention can be used with enzymes or mixtures of enzymes from any type, including but not limited to phytases and other phosphatases, amylases, proteases, lipases and phospholipases, cellulases such as β-glucanases, pectinases, hemicellulases such as xylanases and other plant-cell wall degrading enzymes, esterases, rennets such as fungal proteases or chymosin, and β-galactosidases. It is to be understood that whenever referred to the enzyme or an enzyme, also mixtures of enzymes are included in these terms, irrespecitve of whether such mixtures are obtainable directly in a single fermentation or by mixing enzymes obtainable in different fermentions; and further including enzymes obtainable by fermentation of recombinant organisms. The enzyme is preferably selected from the group comprising fungal phytases, fungal hemicellulases, fungal cellulases and bacterial proteases. More preferably the enzyme is selected from the group comprising phytases and endo-xylanases derivable from a fungus which belongs to the Aspergillus niger Group as defined by Raper and Fennell (1965, In: The Genus Aspergillus, The Williams & Wilkins Company, Baltimore, pp 293–344), β-glucanases and endo-xylanases derivable from a Trichoderma species, and proteases derivable from Bacillus species.

The invention also discloses solid compositions comprising at least one enzyme and an inorganic salt, wherein the dosage of the inorganic salt is at least 5% (w/w) of the weight of the enzyme(s). Preferably the inorganic salt is a salt of a divalent cation, more preferably zinc, magnesium or calcium salt, most preferably zinc or magnesium sulphate. The dosage of the inorganic salt in the composition is at least 5% (w/w), preferably at least 15%, more preferably at least 30%, still more preferably at least 60% and most preferably at least 90% of the weight of the enzyme(s). Enzymes which may be prepared in compositions according to the invention include all those mentioned above. particularly those which are preferred.

In a further embodiment of the invention the above described solid compositions are used to prepare an animal feed. The preparation of animal feed often includes a pelleting step during which a significant amount of enzyme activity can be lost. The use of the solid composition of the invention reduces these losses in enzyme activity during pelleting. Typically an animal feed composition comprises raw materials of vegetable origin providing energy and metabolites for growth. The feed is supplemented with minerals and vitamins and it is common to add animal fat and animal proteins to the feed.

In yet another embodiment of the invention, a solid composition comprising a phytase with a improved storage stability is disclosed. The storage stability of the phytase in this solid composition is such that upon storage during 8 weeks, preferably in a closed container, at 30° C., less than 35%, preferably less than 20%, more preferably less than 10% and most preferably less than 5% of the initial phytase activity is lost. The phytase compositions may comprise an organic or inorganic physiologically acceptable carrier (e.g. grain-based carriers like wheat middlings, wheat flour, rice hulls, and so on, other organic carriers like tapioca, potato starch, cane sugar and so on, inorganic carriers like sodium chloride, potassium sulphate, silica and so on), in combination with phytase enzyme, possibly combined with other enzymes for functionalities' or conveniences' sake, and agents to further improve the products' appearance or functionality with respect to colour, flowing behaviour, physical, chemical or microbial stability, smell, taste, dust formation and so on. The skilled person will understand that similar compositions can be made for feed-enzymes other than phytase.

The following examples are provide by way of illustration of the invention.

EXAMPLES

Example 1

A fungal phytase concentrate (as produced by and obtainable from Gist-brocades) containing approximately 11% of enzyme by weight was split into two portions. To one portion 240 g/l of $MgSO_4.7H_2O$ was added. After dissolution of the salt, resulting in a clear solution, both solutions were spray dried using a Buchi lab scale spray drier with inlet temperature of 130° C. and outlet temperature of 85° C.

The resulting powders were mixed with wheat middlings in a weight ratio of 1:10 to neutralize any differences in water activity between the preparations. After equilibration this was confirmed by measurement of the water activities, which both were found to be 0.45 at room temperature.

The final products were then stored at 30° C. in closed jars and after storage the products were simultaneously analyzed for enzyme activity. After eight weeks of storage the activity loss of the preparation without salt addition amounted to 35%, against only 5% loss for the preparation with salt addition.

Example 2

Into separate portions of a concentrate of a Bacillus-derived alkaline protease (as produced by and obtainable from Genencor International Inc.) containing approximately 12% of enzyme protein by weight, O and 85 g/l of $MgSO_4.0H_2O$ was dissolved. These concentrates were then coated onto sodium sulphate carrier using a Niro STREA-1 lab scale fluid bed coater with inlet-/outlet temperatures of 80° and 50° C., respectively. The activity losses for this process step ware 28% and 14% respectively.

The resulting particles were mixed with a surplus of bleach-containing commercial detergent powder for the European market and incubated in open jars at 35° C. and 55% relative humidity. After 6 weeks of storage the remaining enzyme activity of the preparations was 42% with salt addition and only 30% without.

Example 3

240 g/l of $MgSO_4.7H_2O$ was dissolved into a portion of Trichoderma-derived enzyme concentrate (as produced by and obtainable from Gist-brocades) with a total dry matter content of 25% by weight, containing both a β-glucanase and an endo-xylanase enzyme. The resulting solution and the original concentrate were separately coated onto a sodium sulphate carrier in a Glatt WSG-60 fluid bed coater at inlet-/outlet temperatures of 80° and 50° C., respectively. The process activity losses were 5% and 10% for the β-glucanase and 10% and 25% for the endo-xylanase with and without salt-addition respectively.

The resulting particles were incubated at 30° C. and 62% relative humidity. After 12 weeks of storage the activity losses for the β-glucanase were 10% and undetectable and for the endo-xylanase the activity losses were 10% and 25%, for each enzyme with and without salt addition, respectively.

The granulates were also incorporated in a feed mixture and subjected to a pilot scale pelleting process at a temperature of 70° C. The β-glucanase activity losses amounted to 46% and 59% and the endo-xylanase losses were 37% and 66% with and without salt addition respectively.

The feed mixture used in the pelleting process was composed of;

| Components | % (w/w) |
|---|---|
| Maize | 50.00 |
| Peas (22.9% raw protein) | 3.50 |
| Defatted soy (45.5% raw protein) | 28.00 |
| Tapioca | 2.38 |
| Animal meal (58% raw protein) | 3.60 |
| Fish meal (72.7% raw protein) | 1.00 |
| Hydrolysed feather meal | 1.00 |
| Soy oil | 1.75 |
| Animal fat | 3.50 |
| Vitamin/mineral premix | 3.15 |
| Limestone | 0.86 |
| Monocalcium phosphate | 0.96 |
| Sodium chloride | 0.30 |

Example 4

Different amounts of magnesium sulphate were dissolved in 100 ml of demineralized water after which 100 ml of a fungal phytase concentrate (as produced by and obtainable from Gist-brocades) containing app. 17% by weight of pure enzyme was added to each portion. After mixing the resulting solutions were spray-dried using a lab-scale Buchi 190 Mini Spray Dryer with inlet/outlet temperatures of 140 and 80° C. respectively.

The resulting powders were mixed with wheat middlings in a ratio of 1:9. After equilibration water activity values at 35° C. were measured for control sample and sample with highest salt dosage to exclude water activity effects. The mixtures were subsequently incubated in closed bottles at 35° C. for 8 weeks, after which activity losses were measured.

The results are presented in the following table:

| $MgSO_4$-dosage [g/g enzyme] | Mixture Water Activity [—] | Storage losses after 8 weeks at 35° C. |
|---|---|---|
| 0 | 0.292 | 52% |
| 0.31 | — | 37% |
| 0.61 | — | 26% |
| 1.19 | — | 15% |
| 1.84 | — | 15% |
| 2.38 | 0.303 | 17% |

Example 5

According to the same protocol as mentioned in example 4 different salts in a dosage of 80 mmol per 100 ml of phytase concentrate have been used to produce stabilized enzyme powders. Mixing with wheat middlings and stability testing took place analogously to example 4.

The results are presented in the following table:

| Salt type | Water Activity [—] | Spray Drying losses | Storage losses after 8 weeks at 35° C. |
|---|---|---|---|
| None | 0.29 | 6% | 52% |
| magnesium sulphate | — | 7% | 15% |
| magnesium chloride | 0.30 | 26% | 43% |
| magnesium nitrate | 0.31 | 32% | 27% |
| zinc sulphate | — | 5% | 9% |
| zinc chloride | — | 48% | 5% |
| calcium chloride | — | 40% | 18% |
| calcium nitrate | — | 44% | 13% |
| sodium sulphate | — | 11% | 51% |
| potassium sulphate | — | 17% | 36% |
| ammonium sulphate | — | 6% | 46% |

Example 6

Using the protocol described in Example 5, three phytase containing solutions were prepared containing either no added salt, magnesium sulphate or zinc sulphate. These solutions were subsequently dried using freeze drying instead of spray drying. The freeze drying was accomplished by freezing the mixed enzyme/salt solutions in a flask by submerging the flask in liquid nitrogen, after which high vacuum was applied to remove the water. The resulting dry preparations were crushed in a mortar and mixed with wheat middlings prior to stability testing for 8 weeks at 35° C. in closed bottles. The results are presented in the following Table.

| Salt type | Water activity of mixture | Activity losses after 8 weeks at 35° C. |
|---|---|---|
| None | 0.31 | 46% |
| magnesium sulphate | 0.31 | 16% |
| zinc sulphate | — | 3% |

We claim:

1. A solid enzyme composition which is storage- and processing-stable comprising an enzyme component and a water soluble inorganic salt, wherein the concentration of the inorganic salt is at least 5% (w/w) of the weight of said enzyme component, and wherein said inorganic salt comprises a divalent cation selected from the group consisting of zinc and magnesium, wherein said enzyme component comprises at least one enzyme selected from the group consisting of a phytase, a protease, a hemicellulase, and a mixture of hemicellulase and cellulase, wherein said composition is homogenous with respect to the distribution of the inorganic salt and the enzyme component, and whereby the composition is obtained by:
   a) preparing a solution comprising the enzyme component and the water soluble inorganic salt, wherein the concentration of the inorganic salt is at least 5% (w/w) of the weight of said enzyme component, and
   b) drying the solution of step a) by the removal of water so as to obtain said solid enzyme composition that is stable upon storage and during processing.

2. The solid composition according to claim 1, wherein the composition comprises particles which are homogeneous with respect to the distribution of the inorganic salt and said enzyme component.

3. The solid composition according to claim 1, wherein the composition comprises a carrier coating which is homogeneous with respect to the distribution of the inorganic salt and said enzyme component.

4. The solid enzyme composition according to claim 1, wherein said enzyme component is a phytase and wherein the storage stability of the solid composition comprises a loss of less than 35% of the initial phytase activity during 8 weeks of storage at 30° C.

5. An animal feed comprising the solid enzyme composition according to claim 1.

6. The solid enzyme composition according to claim 1, wherein the inorganic salt comprises a sulphate anion.

7. The solid composition according to claim 1, wherein the drying of the solution containing said enzyme component and the inorganic salt comprises the use of a dryer selected from the group consisting of a spray dryer, a fluid-bed dryer and a freeze dryer.

8. The solid enzyme composition according to claim 1, wherein said enzyme component is selected from the group consisting of: an Aspergillus phytase, a Bacillus protease, an Aspergillus hemicellulase, and a mixture of a Trichoderma hemicellulase and a Trichoderma cellulase.

9. A method for preparing a storage and processing stable solid enzyme composition, comprising the steps of:

a) preparing an aqueous solution comprising an enzyme, wherein said enzyme is selected from the group consisting of: a phytase, a protease, a hemicellulase, and a mixture of a hemicellulase and a cellulase and a water soluble inorganic salt, wherein the concentration of the inorganic salt is at least 5% (w/w) of the weight of the enzyme and wherein the inorganic salt comprises a divalent cation selected from the group consisting of zinc and magnesium, and b) drying the solution of step (a) so as to obtain said solid enzyme composition that is stable upon storage and during processing.

10. The method according to claim 9, wherein the inorganic salt comprises a sulphate anion.

11. The method according to claim 9, wherein the drying of the solution containing the enzyme and the inorganic salt comprises the use of a dryer selected from the group consisting of a spray dryer, a fluid-bed dryer and a freeze dryer.

12. The method according to claim 9, wherein said enzyme component is selected from the group consisting of: an Aspergillus phytase, a Bacillus protease, an Aspergillus hemicellulase, and a mixture of a Trichoderma hemicellulase and a Trichoderma cellulase.

13. A solid enzyme composition prepared by the method of claim 9.

14. A solid enzyme composition prepared by the method of claim 9, wherein said enzyme is a phytase with a storage stability which, upon storage of the solid composition during 8 weeks at 30° C., less than 35% of the initial phytase activity is lost.

15. An animal feed comprising a solid composition as defined in claim 14.

* * * * *

UNITED STATES PATENT AND TRADEMARK OFFICE
CERTIFICATE OF CORRECTION

PATENT NO. : 5,972,669

DATED : October 26, 1999

INVENTOR(S) : Rudolf C.M. BARENDSE *et al.*

It is certified that error appears in the above-identified patent and that said Letters Patent is hereby corrected as shown below:

ON THE TITLE PAGE: item [19], line 2: "Harz et al." should read --Barendse et al.--;
after [75] Inventors: "Hans-Peter Harz, Dedenhofen; Roland Jurgen Betz, Niederkirchen, both of Germany" should read --Rudolf C.M. Barendse, CM Delft, The Netherlands; Hans-Peter Harz, Dedenhofen, Germany; and Roland Jurgen Betz, Niederkirchen, Germany.--

Signed and Sealed this

Fourteenth Day of November, 2000

Attest:

Q. TODD DICKINSON

*Attesting Officer*  *Director of Patents and Trademarks*